United States Patent [19]

Mactaggart

[11] 4,171,918
[45] Oct. 23, 1979

[54] INFRARED MOISTURE MEASURING APPARATUS

[75] Inventor: John W. Mactaggart, Bolton, Canada

[73] Assignee: Sentrol Systems Ltd., Downsview, Canada

[21] Appl. No.: 754,174

[22] Filed: Dec. 27, 1976

[51] Int. Cl.² .............................. G01J 3/46; G01J 3/48
[52] U.S. Cl. ..................................... 356/408; 356/425; 356/419; 250/238; 250/339
[58] Field of Search ................. 356/179, 195, 51, 189, 356/214 C, 188; 250/339, 341, 238, 352

[56] References Cited

U.S. PATENT DOCUMENTS

| | | | |
|---|---|---|---|
| 3,467,475 | 9/1969 | Celio et al. | 356/188 |
| 3,661,462 | 5/1972 | Natens | 356/188 X |
| 3,793,522 | 2/1974 | Coleby et al. | 250/238 X |
| 3,853,407 | 10/1974 | Dewey | 356/189 |
| 3,878,107 | 4/1975 | Pembrook et al. | 356/188 X |
| 3,936,637 | 2/1976 | Reine et al. | 250/352 |
| 4,006,358 | 2/1977 | Howarth | 356/51 |

*Primary Examiner*—Vincent P. McGraw
*Assistant Examiner*—Rodney B. Bovernick
*Attorney, Agent, or Firm*—Shenier & O'Connor

[57] ABSTRACT

Apparatus for determining the content of moisture or other substance in a material by measuring its relative reflectance at two infrared wavelengths. A chopped radiation beam is produced by arranging a tuning fork such that an oscillating element alternatively moves first and second spaced optical bandpass filters having first and second passband wavelengths into position to intercept a beam of source radiation. The chopped beam is directed on the material being analyzed, and radiation reflected therefrom is applied to a radiation detector. The relative transmittances of the filters at their passband wavelengths are such that the radiation detector generates alternating pulses of equal amplitude for a material having a specified content of the substance. The tuning fork also includes a third filter of zero transmittance which periodically interrupts the beam of source radiation so that the detector provides a background signal which is used to correct the amplitudes of the alternating pulses. The alternating pulses are separated and applied to a ratio-determining circuit. The output from the detector is also applied a feedback circuit regulating the temperature of the detector.

4 Claims, 7 Drawing Figures

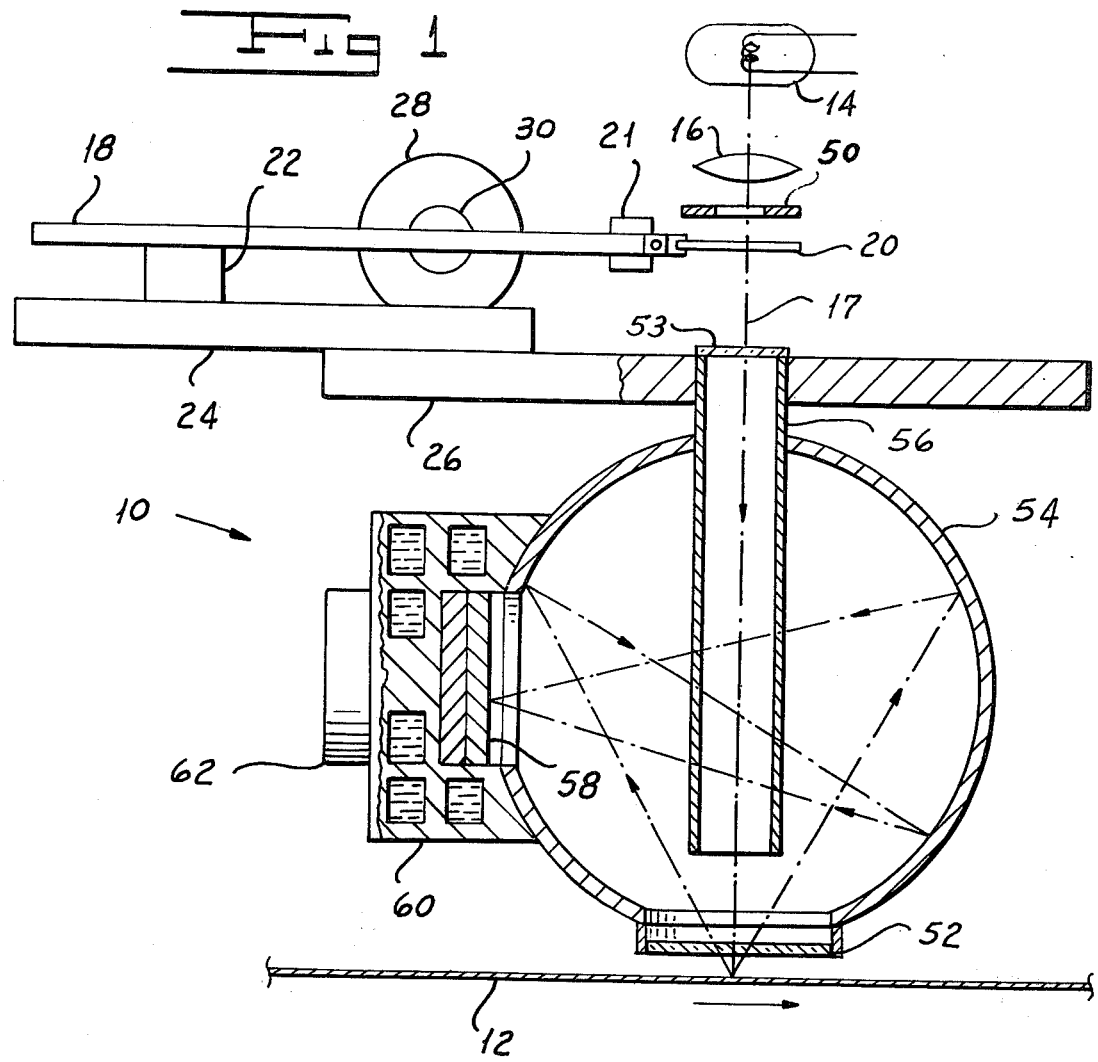
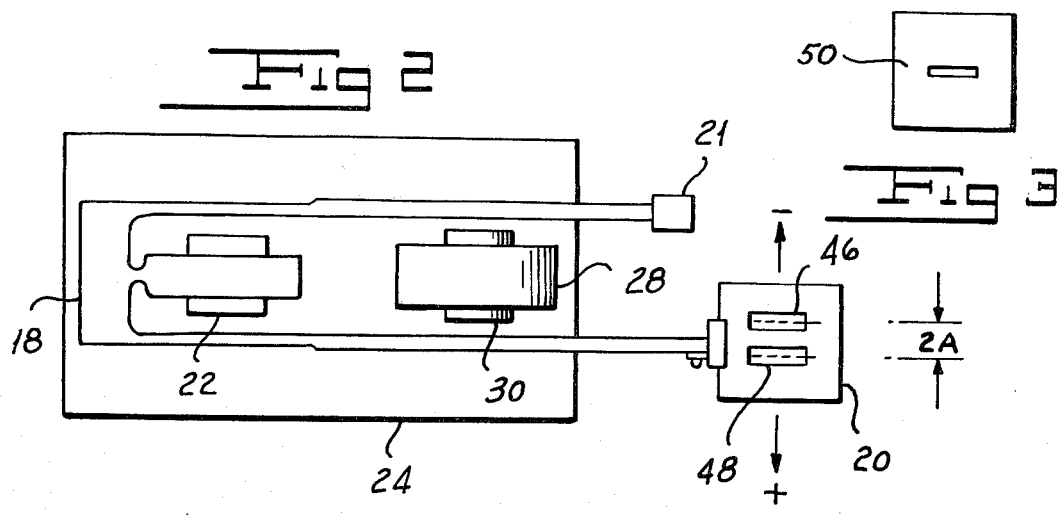

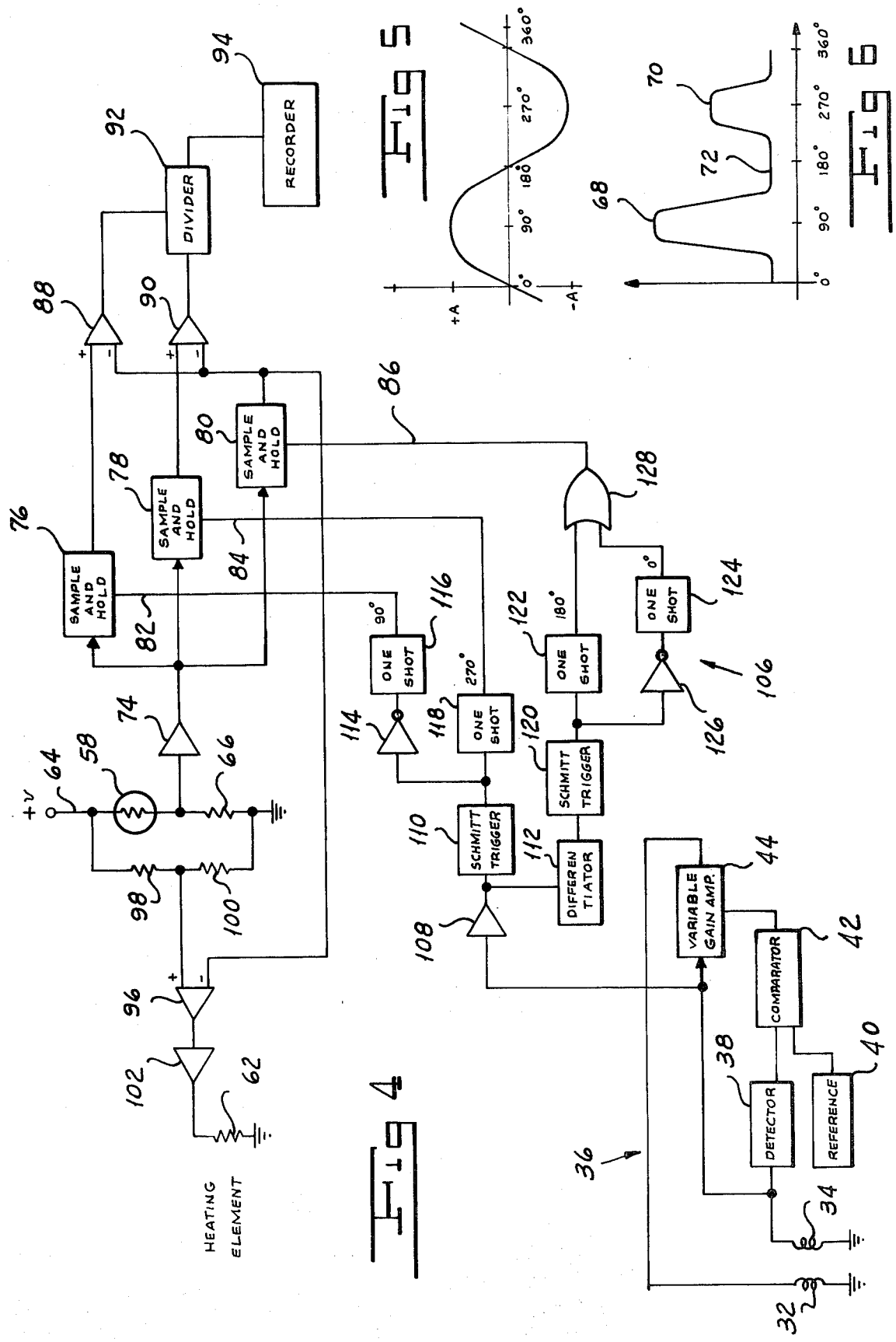

INFRARED MOISTURE MEASURING APPARATUS

BACKGROUND OF THE INVENTION

This invention relates to apparatus for radiation absorption measurement and, more particularly, to apparatus for determining the moisture content of a moving web of material by measuring the relative reflectance of two beams of infrared radiation.

A well-known method for determining the content of a substance such as water in a material involves the measurement of relative infrared reflectance. At certain characteristic wavelengths corresponding to resonance of a particular substance, the absorption, and thus reflectance, of the material being analyzed varies considerably with the content of the substance, while at other wavelengths not coinciding with a resonant wavelength, the degree of absorption is relatively insensitive to changes in material composition. By measuring the ratio of the reflectance of the material at resonant and nonresonant wavelengths, the content of the substance can be determined simply and rapidly. In many practical applications of this technique, both the resonant-wavelength beam and the nonresonant-wavelength or reference beam are derived from a single radiation source using a chopping wheel to obtain alternating pulses of radiation. One such implementation is shown in U.S. Pat. No. 3,150,264, issued to R. C. Ehlert.

Systems of the type described above are often used in on-line applications to measure the moisture content of webs of paper pulp or the like. Such systems, however, are susceptible to errors resulting from the nonlinearity inherent in any practical detector used to sense infrared radiation. Because of this nonlinearity, the reflectance measurement is sensitive to spurious sources of infrared radiation such as the moving web itself, which may be as hot as 300° F. Variations in the absolute amplitudes of the reflected resonant and nonresonant radiation pulses due to sheet flutter and the like will also affect the measurement, even though the amplitudes of the respective pulses vary proportionately. Finally, the nonlinearity of the detector makes the reflective ratio measurement sensitive to changes in operating point due to changes in the ambient temperature.

Error may also result when the sheet flutter contains frequency components near the chopping frequency, which is typically about 10 Hz. Since the apparatus cannot distinguish between amplitude variations due to sheet flutter and those due to changes in material composition, the measured reflectance ratio will contain a spurious component at a frequency equal to the difference between the flutter frequency and the chopping frequency.

SUMMARY OF THE INVENTION

One object of my invention is to provide a moisture measuring apparatus which may be used to measure moisture in a rapidly moving web.

Another object of my invention is to provide a moisture measuring apparatus which is insensitive to spurious sources of radiation and changes in ambient temperature.

A further object of my invention is to provide a moisture measuring apparatus which is insensitive to web flutter.

Other and further objects will be apparent from the following description;

In general, my invention contemplates apparatus for analyzing a material by measuring relative infrared reflectance in which a chopped radiation beam is produced by arranging a tuning fork such that an oscillating element alternately moves first and second spaced optical bandpass filters into position to intercept a beam of source radiation. The chopped beam is directed on the material being analyzed so that a detector receptive to radiation reflected from the material generates spaced apart pulses corresponding to the radiation pulses. The relative transmittances of the filters are such that the radiation detector generates alternating pulses of equal amplitude for a material having some standard or specified composition.

By using a tuning fork rather than a motor-driven chopping wheel such as used in the prior art, I can attain a substantially higher chopping frequency and thus greatly reduce the sensitivity of the apparatus to sheet flutter, since the sheet movement in any one chopping cycle due to sheet flutter is minimal. In addition, the absence of any wearing surfaces gives the tuning fork obvious mechanical advantages over shaft-driven chopping wheels of the prior art.

Further, by choosing filter transmittances to provide alternating reference and resonant-wavelength pulses of equal amplitude for a material having some standard content of moisture, for example, I effectively minimize errors due to nonlinearity in the radiation detector. Deviations in the content of the material from the norm are translated into deviations in the ratio of the amplitudes of the alternating pulses from unity. Such extraneous influences as sheet flutter and stray or external radiation produce negligible error in the amplitude ratio if such ratio is close to unity. This is especially important in systems in which the moisture content measurement is used for feedback control.

In another aspect, my invention contemplates an improved system for controlling the temperature of the radiation detector to govern its operating point. Prior art systems have typically used a temperature sensor, separate from the radiation detection, which is coupled to a suitable feedback temperature control. The temperature control receives no input from the radiation detector itself. As a result, random variations in manufacture produce corresponding variations in the "dark" current and hence the operating point of such detectors, resulting in unreliable operation. My apparatus avoids this defect inherent in prior art systems by using the detector signal itself as a composite indication of the temperature of the detector and of the magnitude of stray radiation from the hot web. By using the detector itself rather than a separate sensor to control temperature, I directly control the operating point of the radiation detector and hence reduce errors in the measurement of amplitude ratios differing appreciably from unity.

BRIEF DESCRIPTION OF THE DRAWINGS

In the accompanying drawings to which reference is made in the instant specification and in which like reference characters are used to indicate like parts in the various views:

FIG. 1 is a side elevation, shown partly in section, of my moisture measuring apparatus.

FIG. 2 is a top plan view of the tuning fork.

FIG. 3 is a top plan view of the optical slit.

FIG. 4 is a schematic diagram of the signal processing portion of my apparatus.

FIG. 5 is a graph of the displacement of the tuning fork tines as a function of phase angle.

FIG. 6 is a graph of a typical waveform generated by the radiation detector.

DETAILED DESCRIPTION OF THE PREFERRED EMBODIMENT

Figure 7:
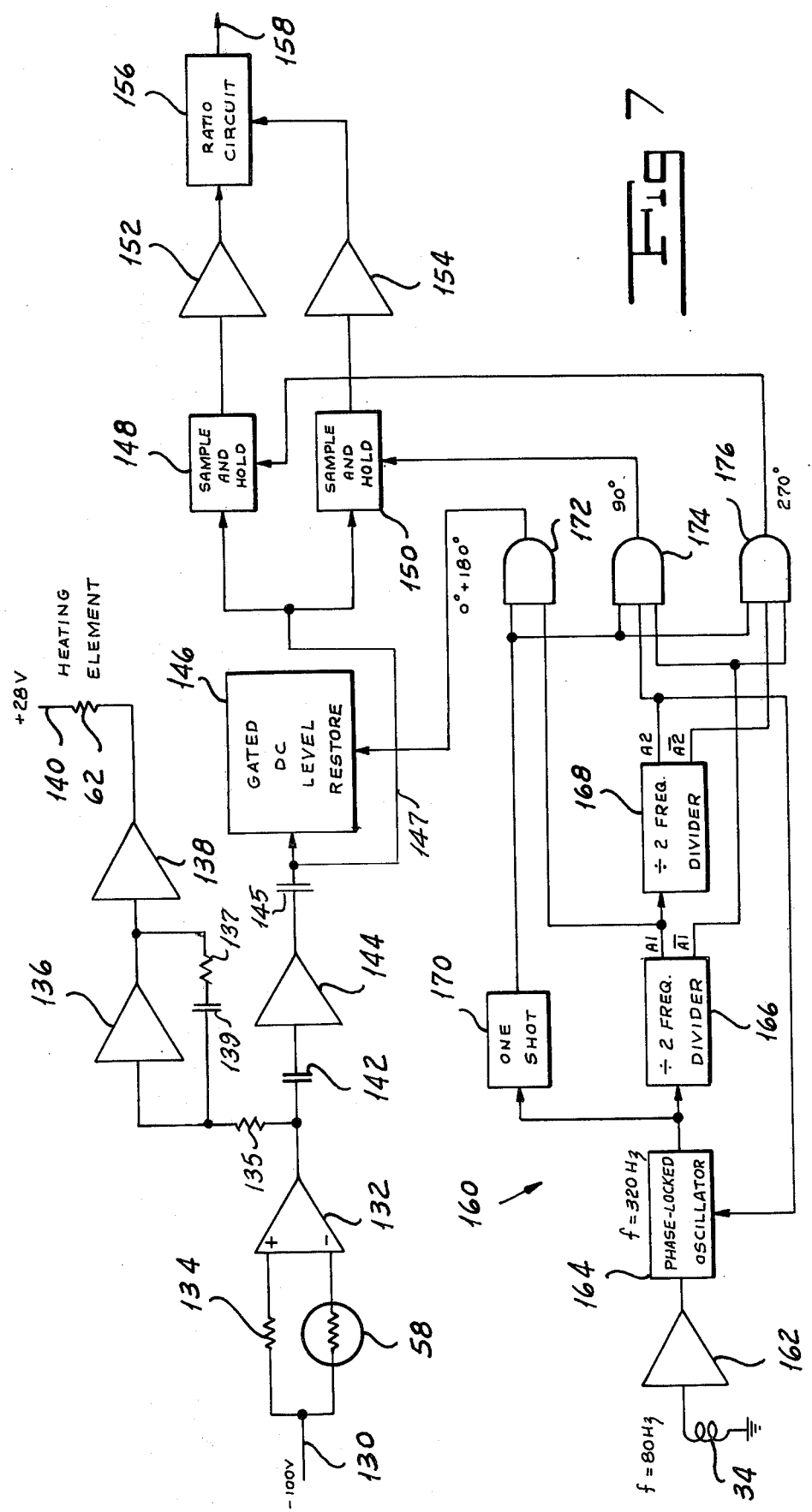
FIG. 7 is a schematic diagram of an alternative signal-processing circuit for my apparatus.

Referring to the drawings, my moisture measuring apparatus, indicated generally by the reference numeral 10, is disposed facing the surface of a moving web 12 of paper or the like. A collimating lens 16 directs radiation from an incandescent bulb 14 or other suitable source onto the surface of the web 12 along a radiation path 17. A tuning fork 18 with a resonant frequency of 80 Hz and having an opaque filter mount 20 attached to one of its tines is arranged with the filter mount 20 intercepting the radiation path 17. A counterweight 21 is attached to the other tine to balance the tuning fork 18. A spacer 22 separates the tuning fork 18 from a supporting member 24 mounted on a frame 26. Disposed between the tines is a coil assembly 28 wound on a permanent magnet core 30. The coil assembly 28 comprises a drive coil 32 and a pickup coil 34 (FIG. 4).

Pickup coil 34 is coupled to a tuning fork control circuit indicated generally by the reference numeral 36. In the control circuit 36, a detector 38 coupled to the pickup coil 34 provides a signal representing the envelope of the pickup coil signal. The envelope signal from detector 38 is fed together with a reference signal from a source 40 to a comparator 42. The output of the comparator 42 is connected to the gain control input of a variable-gain amplifier 44. Pickup coil 34 is connected to the signal input of amplifier 44. The output of amplifier 44 is connected to drive coil 32.

The control circuit 36 ensures a constant amplitude of vibration of the tunning fork 18. When the apparatus is first turned on, the output from coil 34, and thus detector 38, is zero. Comparator 42 provides maximum gain from amplifier 44, and oscillations build up. When the output signal from detector 38 becomes substantially equal to the reference signal 40, comparator 42 reduces the gain of amplifier 44 to a value sufficient to sustain oscillation at the desired amplitude, determined by reference 40.

The filter mount 20 holds two spaced, parallel slit-shaped filters 46 and 48. The filters are arranged such that they intercept the radiation path 17 when the tuning fork tine carrying the filter mount 20 reaches its maximum displacement from equilibrium position. A fixed slit 50 arranged parallel to the slits 46 and 48 is disposed in the radiation path 17. The width of slit 50 is less than that of filters 46 and 48 to ensure that the amplitude of the transmitted beam is relatively insensitive to variations in the amplitude of vibration of the tuning fork 18.

The filters 46 and 48 are selected to pass respectively radiation having a reference wavelength different from any resonant wavelength of the substance being measured and radiation corresponding to a resonant wavelength of such substance. In a typical application involving moisture measurement in a paper web, reference wavelength filter 46 may have a passband wavelength of 1.81 microns, while resonant-wavelength filter 48 may have a passband wavelength of 1.94 microns. Assuming that the desired or normal moisture content is about 18%, the transmittance of resonant-wavelength filter 48 should be about 25% higher than that of the reference filter 46. For higher or lower desired moisture contents, the 25% figure should be raised or lowered proportionately.

Reflected radiation from the web 12 passes through an infrared-transmissive quartz window 52 and is collected by an integrating sphere 54 arranged concentrically with the incident radiation path 17. Integrating sphere 54 is formed with a diffusely reflective inner surface such as spun aluminum which has been roughened by grit blasting or the like. A cylindrical shield 56 arranged coaxially with the incident radiation path 17 prevents interaction between the incident and reflected radiation and ensures that no incident radiation impinges on the inner surface of the sphere 54. A lead sulfide detector 58 disposed to one side of sphere 54, as seen in FIG. 1, senses the reflected radiation after it has been diffused by the inner surface of sphere 54. The detector 58 is cooled by a surrounding water jacket 60 through which water or other liquid is pumped and is simultaneously heated by a heating element 62 which is controlled in a manner to be described. Preferably, the interior of the sphere 54 is pressurized with dry nitrogen gas to eliminate inaccuracies due to changes in the relative humidity and to protect the optical and mechanical components. Accordingly, shield 56 is provided with a quartz window 53.

One terminal of detector 58 is connected to a line 64 supplying a constant DC voltage. The other terminal of detector 58 is coupled to ground through a temperature-compensated resistor 66. The output of detector 58 at its junction with resistor 66 comprises a series of alternating pulses 68 and 79 (FIG. 5) corresponding respectively to the intensity of the reflected radiation at the reference and resonant wavelengths and include a relatively constant "background" signal 72 corresponding to the detector output in the absence of any incident radiation. Pulses 68 and 70 occur respectively at maximum positive and negative displacement of the tuning fork tines (FIG. 2), when respective filters 46 and 48 are in position to intercept the radiation path 17. For illustrative purposes only, I have shown the amplitude of reference pulse 68 to be appreciably greater than that of resonant-wavelength pulse 70, as would be the case if filters 46 and 48 were to have substantially equal transmittances. However, as previously pointed out, filter 46 has less transmittance to approximate the attenuation due to absorption in the resonant-wavelength beam. The background signal 72 is observable when the tuning fork tines are at their equilibrium position; the radiation path 17 is blocked by the opaque filter mount 20. The opaque portion of filter mount 20 disposed between the filters should have a width greater than that of aperture slit 50 to insure complete interruption of the incident beam. The detector output is connected to a buffer amplifier 74. Sample-and-hold circuits 76, 78, and 80 sample the output of buffer amplifier 74 at discrete instants in the operating cycle. More particularly, a line 82 enables circuit 76 with a sampling pulse at 90°, or maximum positive displacement, so that circuit 76 provides an output corresponding to the reference-wavelength pulse 68. Similarly, a line 84 enables circuit 78 at 270°, or maximum negative displacement, so that circuit 78 provides an output corresponding to the resonant-wavelength pulse 70. A third line 86 enables circuit 80 at 0° and 180°, or zero displacement of the fork tines, so that circuit 80 provides an output corresponding to the background signal 72. Sample-and-hold circuits 76 and 80 drive respective positive and negative inputs of a differential amplifier 88 to provide a corrected reference-wavelength signal compensated for the background signal 72. Similarly, sample-and-hold circuits 78 and 80 drive the respective positive and negative inputs of a differential amplifier 90 to provide a corrected resonant-wavelength signal compensated for the background signal 72. A divider circuit 92 responsive to the outputs of amplifiers 88 and 90 provides an output representing the ratio of the two signals. The output of circuit 92 is fed to a graphic or other recorder 94 and may be used to drive a suitable feedback control circuit (not shown).

The background component derived by circuit 80 also provides a signal for controlling the electrical power supplied to the heating element 62. More particularly, the output of circuit 80 is coupled to the negative input of a differential amplifier 96. The positive input of amplifier 96 is coupled to the common terminal of temperature-compensated resistors 98 and 100 which are series-connected between ground and line 64. The output of differential amplifier 96 is coupled to a power amplifier 102 which drives the heating element 62. Resistors 98, 100, and 66, in conjunction with detector 58, form a bridge circuit. The bridge circuit is nulled by controlling the temperature of detector 58. Any increase in the amplitude of the background signal 72, due to an increase in temperature of either the detector or the web, results in an increased output from sample-and-hold circuit 80. This increased output in turn decreases the output from differential amplifier 96. As a result, amplifier 102 supplies less power to heating element 62 and allows the detector 58 to be cooled by the water jacket 60. Similarly, any decrease in the amplitude of the background signal 72 due to a decrease in temperature will cause more power to be supplied to the heating element 62 and thus raise the temperature of the detector 58.

The sampling pulses on lines 82, 84, and 86 are derived by a pulse generator circuit indicated generally by the reference numeral 106. In this circuit, a buffer amplifier 108 responsive to the pickup coil 34 drives a Schmitt trigger 110 and a differentiator 112. Schmitt trigger 110 drives a one-shot multivibrator 118 which produces an output pulse whenever the output of amplifier 108 changes from negative to positive. Schmitt trigger 110 also drives a second one-shot multivibrator 116 through an inverter 114. Differentiator 112 drives a Schmitt trigger 120. Schmitt trigger 120 in turn drives a one-shot multivibrator 122 directly and a second one-shot multivibrator 124 through an inverter 126. Multivibrator 122 provides an output pulse whenever the output of differentiator 112 changes from negative to positive. One-shot multivibrators 122 and 124 are each coupled to inputs of an OR gate 128.

The output of the pickup coil 34 is a cosine signal proportional to the time derivative of the displacement plotted in FIG. 5. Amplifier 108 provides this cosine signal to Schmitt trigger 110 and differentiator 112. Differentiator 112 further differentiates the cosine signal to provide an inverted sine signal to Schmitt trigger 120. At 180° in the oscillation cycle, when the fork tines are at their equilibrium position, the inverted sine signal from differentiator 112 changes from positive to negative, causing an output pulse from multivibrator 122 which is coupled through OR gate 128 to line 86. Similarly, at 0°, with the fork tines at equilibrium position, inverter 126 causes multivibrator 124 to provide a pulse which is also coupled through OR gate 128 to line 86. When, at 270°, the fork tines reach their maximum negative displacement, the cosine signal provided by amplifier 108 changes from negative to positive; and multivibrator 118 provides a pulse on line 84. Similarly, at 90°, when the fork tines reach maximum negative displacement, inverter 114 causes multivibrator 116 to provide a pulse on line 82. OR gate 128 thus provides a pulse on line 86 whenever the fork tines pass through their equilibrium position, while one-shot multivibrators 116 and 118 provide pulses on lines 82 and 84 whenever the fork tines reach their maximum positive and negative displacements, respectively.

In the circuit shown in FIG. 4, the temperature control signal is derived by sampling the detector output during the dark period. In practice, the peak amplitude of the reference-wavelength pulse 68 and the resonant-wavelength pulse 70 are sufficiently constant over a long period of time that the heating element 62 can be controlled by a signal that is simply the time average of the detector output. In FIG. 7, I show an alternative signal-processing circuit in which the detector output is used directly to control the heating element 62. More particularly, the detector 58 is coupled between a line 130 providing a DC potential of $-100$ volts and the negative input of a differential amplifier 132. The positive input of the amplifier 132 is coupled to a temperature-compensated resistor 134, the other terminal of which is coupled to line 130. The detector 58 and the resistor 134 in effect form the lower half of a balanced bridge, the upper half being formed by the internal resistance of each of the inputs of amplifier 132. Amplifier 132 is coupled through a resistor 135 to the input of a high-gain inverting operational amplifier 136. The output of amplifier 136 is fed to an inverting power amplifier 138 as well as back to its input through a resistor 137 connected in series with a capacitor 139. The values of capacitor 139 and resistor 135 are such as to produce a time constant of about 30 seconds. Amplifier 136 thus essentially acts as an integrator. Resistor 137 causes amplifier 136 to produce some proportional output to insure stability of the heater control circuit. Power amplifier 138 is coupled to one terminal of the heating element 62, the other terminal of which is coupled to a line 140 providing a DC potential of $+28$ volts.

The above-described circuit constitutes a negative feedback system for controlling the temperature of heating element 62. Any rise in the temperature of the detector 58 will result in a corresponding decrease in the resistance of the detector. As a result, the signal applied to the negative input of amplifier 132 becomes more negative. Amplifier 132 thus provides a more positive output, causing amplifier 138 to provide a more positive output and thus decreasing the power applied to the heating element 62. Similarly, any decrease in temperature of the detector 58 will produce a less positive output from amplifier 138, thus increasing the power supplied to heating element 62.

Differential amplifier 132 is also coupled to the portion of the signal-processing circuit which recovers the reference-wavelength pulse 68 and the resonant-wavelength pulse 70. More particularly, amplifier 132 drives a noninverting buffer amplifier 144 through a blocking capacitor 142. The output of amplifier 144, constituting a zero-time-average AC signal having the same wave form as shown in FIG. 6, is applied through a restoring capacitor 145 to a gated DC level restoring circuit 146. Circuit 146 may be of a conventional type in which a normally nonconductive, or disabled, gate is selectively enabled by AND circuit 172 to couple line 147 momentarily to ground. Gating pulses applied to the gate input of circuit 146 at 0° and 180° in the oscillation cycle charge capacitor 145 to the level attained by the signal during the dark period. Capacitor 145 thus provides an offset voltage sufficient to restore the level of the signal during the dark period to zero. The signal on line 147 thus has a wave form identical to that shown in FIG. 6, but with a sufficient offset to produce a zero output during the dark periods between pulses.

Circuit 146 drives a pair of sample-and-hold circuits 148 and 150, which are gated at 270° and 90° in the oscillation cycle to recover the reference-wavelength and resonant-wavelength signals, respectively. Sample-and-hold circuits 148 and 150 drive respective noninverting amplifiers 152 and 154. Amplifier 152 is connected to the numerator input of a ratio-determining circuit 156, the denominator input of which is supplied by circuit 154. Circuit 156 provides a ratio signal on line 158 which may be coupled to a suitable control system or to a recorder.

The signal-processing circuit also includes a gate pulse generating circuit indicated generally by the reference numeral 160. In circuit 160 a noninverting buffer amplifier 162 responsive to the pickup coil 34 drives one input of a phase-locked oscillator circuit 164. Oscillator circuit 164 is of a conventional type having an internal voltage-controlled oscillator responsive to a control signal from an internal phase-sensitive detector. The oscillator portion of circuit 164 is tuned to a nominal frequency of 320 Hz, or four times the frequency of the tuning fork 18. The phase-sensitive detector portion receives one input from amplifier 162 and another input from an A2 output of a frequency divider 168.

The output of circuit 164 drives a frequency divider 166 which divides the input frequency by a factor of two. Circuit 166, which may comprise a D-type flip-flop, has a normal output A1 and an inverted output $\overline{A1}$. Circuit 166 changes state in response to positive-going transitions of the signal provided by oscillator 164. The normal output of circuit 166 drives the second frequency divider 168, which also may comprise a D-type flip-flop, and which divides the input frequency by another factor of two. Circuit 168 has a normal output A2 and an inverted input $\overline{A2}$. Like circuit 166, circuit 168 changes state in response to positive-going transitions at its input. The normal output A2 of frequency divider 168 comprises an 80 Hz square wave which, as previously indicated, provides the other input to the phase-sensitive detector portion of circuit 164.

The phase-sensitive detector portion of circuit 164 provides a control signal corresponding to the time average of the product of its inputs. The oscillator portion of circuit 164 decreases or increases its frequency in response to positive and negative control signals, respectively, so that, at equilibrium, the A2 signal lags the output from amplifier 162 by 90° phase. Circuit 168 thus changes to logic 1 and 0 at 0° and 180°, respectively. Circuit 166 thus changes to logic 1 at 0° and 180° and to logic 0 at 90° and 270°, while circuit 164 produces an output that changes from negative to positive at integral multiples of 90° phase as defined in FIG. 6.

Circuits 166 and 168 gate the output of a one-shot circuit 170, coupled to oscillator circuit 164, to produce a pulse at integral multiples of 90°. Thus, at 0°, circuits 166 and 168 provide A1 and A2 outputs of logic 1 to gate the one-shot pulse through AND gate 172, which provides a gating pulse to circuit 146. At 90°, circuits 166 and 168 provide respective $\overline{A1}$ and A2 outputs of logic 1 to gate the one-shot pulse through AND gate 174 to enable sample-and-hold circuit 150. At 180°, circuits 166 and 168 provide respective A1 and A2 outputs of logic 1 to gate the one-shot pulse through AND gate 172 again. Finally, at 270°, counters 166 and 168 provide A1 and A2 outputs of logic 1 to gate the one-shot pulse through AND circuit 176 to enable sample-and-hold circuit 148.

It will be understood that certain features and subcombinations are of utility and may be employed without reference to other features and subcombinations. This is contemplated by and is within the scope of my claims. It is further obvious that various changes may be made in details within the scope of my claims without departing from the spirit of my invention. For example, while the filters 46 and 48 are preferably disposed as shown in the radiation path between the source 14 and the web 12, the filters need not be so disposed and may, if desired, be disposed in the reflected radiation path between the web 12 and the detector 58. Also, while transmission-type filters are used in the embodiment shown, it will be appreciated that reflectance-type filters could also be used. It is, therefore, to be understood that my invention is not to be limited to the specific details shown and described.

Having thus described my invention, what I claim is:

1. Apparatus for measuring deviations from a predetermined value of a property of material including in combination a source of radiation, a radiation detector providing an output, means for coupling radiation from the source to the detector along a path affected by said material, a first radiation filter having a first transmittance, a second radiation filter having a second transmittance, means for sequentially introducing the first and second filters in said path to provide respective first and second outputs from the detector, the first and second filters being constructed with such transmittances that the first and second outputs from the detector are substantially equal when the material has said predetermined property value.

2. Apparatus for measuring deviations in the moisture content of a material from a predetermined moisture content including in combination a source of radiation, a radiation detector providing an output, means for coupling radiation from the source to the detector along a path affected by said material, a first radiation filter having a relatively high transmittance at a water-resonant wavelength, a second radiation filter having a relatively low transmittance at said water-resonant wavelength, means for sequentially introducing the first and second filters in said path to provide respective first and second outputs from the detector, the first and second filters being constructed with such transmittances that the first and second outputs from the dectector are substantially equal when the material has said predetermined moisture content.

3. Apparatus for measuring a property of a material including in combination a source of radiation, a temperature-sensitive radiation detector providing an output, means including a radiation modulator for coupling radiation from the source to the detector along a path affected by said material, means providing a reference signal, means for comparing the detector output with the reference signal, and means responsive to the comparing means for gradually changing the temperature of the radiation detector in such direction as to bring its output to substantial equality with the reference signal.

4. Apparatus for measuring a property of a material including in combination a source of radiation, a temperature-sensitive radiation detector providing an output, means including a radiation modulator for coupling radiation from the source to the detector along a path affected by the said material, means for periodically sampling the output of the detector, means providing a reference signal, means for comparing the sampled detector output with reference signal, and means responsive to the comparing means for gradually changing the temperature of the radiation detector in such direction as to bring its sampled output to substantial equality with the reference signal.

* * * * *